(12) United States Patent
Kim et al.

(10) Patent No.: US 12,115,200 B2
(45) Date of Patent: Oct. 15, 2024

(54) LACTIC ACID BACTERIA AND USE THEREOF

(71) Applicants: UNIVERSITY-INDUSTRY COOPERATION GROUP OF KYUNG HEE UNIVERSITY, Gyeonggi-do (KR); NAVIPHARM CO.,LTD., Gyeonggi-do (KR)

(72) Inventors: Dong-Hyun Kim, Seoul (KR); Myung Joo Han, Seoul (KR)

( * ) Notice: Subject to any disclaimer, the term of this patent is extended or adjusted under 35 U.S.C. 154(b) by 522 days.

(21) Appl. No.: 17/290,516

(22) PCT Filed: Apr. 30, 2019

(86) PCT No.: PCT/KR2019/005239
§ 371 (c)(1),
(2) Date: Apr. 30, 2021

(87) PCT Pub. No.: WO2020/091166
PCT Pub. Date: May 7, 2020

(65) Prior Publication Data
US 2023/0181657 A1    Jun. 15, 2023

(30) Foreign Application Priority Data

Nov. 1, 2018   (KR) .......................... 1020180132834

(51) Int. Cl.
*A61K 35/745* (2015.01)
*A61K 35/747* (2015.01)
(Continued)

(52) U.S. Cl.
CPC .......... *A61K 35/745* (2013.01); *A61K 35/747* (2013.01); *A61P 3/04* (2018.01);
(Continued)

(58) Field of Classification Search
CPC ... A61K 35/747; A61K 35/745; A23L 33/135; A61P 25/24; A61P 3/04; A61P 19/10; C12N 1/20; C12R 2001/25
See application file for complete search history.

(56) References Cited

U.S. PATENT DOCUMENTS 11,202,811 B2    12/2021   Kim
2016/0067289 A1    3/2016   Berggren et al.
(Continued)

FOREIGN PATENT DOCUMENTS

CA    2998841    3/2017
JP    9194384    7/1997
(Continued)

OTHER PUBLICATIONS

Castelo-Branco et al., Maturitas, 52S:S46-S52 (2005) (Year: 2005).*
(Continued)

*Primary Examiner* — Thomas J. Visone
(74) *Attorney, Agent, or Firm* — Wood Phillips Katz Clark & Mortimer

(57) ABSTRACT

The present disclosure relates to *Lactobacillus plantarum* NK3 and *Bifidobacterium longum* NK49, which are novel lactic acid bacteria, and, more particularly, to a composition comprising novel lactic acid bacteria that are useful for the prevention or treatment of female menopausal disorders.

8 Claims, 8 Drawing Sheets
Specification includes a Sequence Listing.

(51) Int. Cl.
    *A61P 3/04*     (2006.01)
    *A61P 19/10*     (2006.01)
    *A61P 25/24*     (2006.01)
    *C12N 1/20*     (2006.01)
    *A61K 35/00*     (2006.01)
    *C12R 1/25*     (2006.01)

(52) U.S. Cl.
    CPC ............... *A61P 19/10* (2018.01); *A61P 25/24* (2018.01); *C12N 1/20* (2013.01); *A61K 2035/115* (2013.01); *C12R 2001/25* (2021.05)

(56) References Cited

U.S. PATENT DOCUMENTS

| | | | |
|---|---|---|---|
| 2016/0074443 | A1 | 3/2016 | Kim |
| 2019/0070229 | A1 | 3/2019 | Choi |
| 2021/0260140 | A1 | 8/2021 | Kim |

FOREIGN PATENT DOCUMENTS

| | | |
|---|---|---|
| KR | 1020150133284 | 11/2015 |
| KR | 1020160007608 | 1/2016 |
| KR | 1020160085235 | 7/2016 |
| KR | 1020160098149 | 8/2016 |
| KR | 101690738 | 12/2016 |
| KR | 101709246 | 2/2017 |
| KR | 1020170032848 | 3/2017 |
| KR | 1020170054682 | 5/2017 |
| KR | 10171750468 | 6/2017 |
| KR | 10171784847 | 9/2017 |
| WO | WO2014163568 | 10/2014 |
| WO | WO2014184643 | 11/2014 |
| WO | WO2015122717 | 8/2015 |
| WO | WO2017037089 | 3/2017 |
| WO | WO2017196006 | 11/2017 |

OTHER PUBLICATIONS

Martinus et al., J. Gen. Pro. DVI, 3( );86-92 (2016) (Year: 2016).*
Parvaneh et al., Biomedic. Res. Internat., 897639:1-10 (2015) (Year: 2015).*
Xu et al., Bone Res., 5(17046):1-18 (2017) (Year: 2017).*
Li et al., J. Clin. Invest., 126(6):2049-2063 (2016) (Year: 2016).*
RU Office Action in Russian Appln. No. 2021112814, dated May 12, 2022, 22 pages (with English Translation).
Santoro et al., "Menopausal symptoms and their management," Endocrinology and Metabolism Clinics North Am., 2015, 44(3):497-515.
EP Extended Search Report in EP Appln. No. 19877635.3, dated Jan. 31, 2022, 6 pages.
CA Office Action in Canadian Appln. No. 3081210, dated Apr. 8, 2022, 4 pages.
Kim et al., "Effects of *Lactobacillus plantarum* and *Bifidobacterium longum* on bacterial vaginosis and ovariectomized osteoporosis in mice," Thesis for the Degree of Master Pharmacy, Department of Life and Nanopharmaceutical Sciences, Graduate School of Kyung Hee University, Feb. 2019, pp. 1-42.
Kim et al., "Lactobacillus plantarum NK3 and *Bifidobacterium longum* NK49 ameliorated *Gardnerella vaginalis*-induced vaginosis in mice," 2017 Fall International Convention of The Pharmaceutical Society of Korea, Oct. 2017, 3 pages.
Kim et al., "Bifidobacterium longum NK49 ameliorated Gardnerella vaginalis-induced vaginosis in mice," 2017 Fall International Convention of The Pharmaceutical Society of Korea, Sponsored by the Korean Federation of Science and Technology Societies, Abstract P5-13, Oct. 2017, p. 530.
Webster's New Riverside University Dictionary, The Riverside Publishing Company, 1984, p. 933.
Collins et al., "The potential of probiotics as a therapy for osteoporosis", Microbiology Spectrum, Aug. 2017, 5(4):1-16.
Korean Notice of Reason for Refusal in KR Appln. No. 1020180132834, dated Oct. 29, 2019, 7 pages with English Translation.
KR Decision to Grant for App No. KR 10-2018-0132834, dated Jul. 22, 2020 (with English Translation) (7 pages).
PCT International Preliminary Report on Patentability in International Appln. No. PCT/KR2018/004590, dated May 5, 2020, 16 pages with English Translation.
PCT International Preliminary Report on Patentability in International Appln. No. PCT/KR2019/005239, dated Apr. 27, 2021, 14 pages with English Translation.
PCT International Search Report and Written Opinion in International Appln. No. PCT/KR2018/004590, dated Feb. 15, 2019, 21 pages with English Translation.
PCT International Search Report and Written Opinion in International Appln. No. PCT/KR2019/005239, dated Aug. 16, 2019, 23 pages with English Translation.
Tabrizi et al., "Prevalence of Gardnerella Vaginalis and Atopobium Vaginae in Virginal Women", Sexually Transmitted Diseases, Nov. 2006, 33(11):663-665.
Wallace et al., "The effects of probiotics on depressive symptoms in humans: a systematic review", Annals of General Psychiatry, 2017, 16(14):1-10.
Whitman et al., "Bacteria and the Fate of Estrogen in the Environment", Cell Chemical Biology, 2017, 24(6):652-653.

* cited by examiner

LACTIC ACID BACTERIA AND USE THEREOF

TECHNICAL FIELD

The present disclosure relates to *Lactobacillus plantarum* NK3 and *Bifidobacterium longum* NK49, which are novel lactic acid bacteria and, more particularly, to a composition comprising novel lactic acid bacteria that are useful for prevention and treatment of female menopausal disorders.

BACKGROUND

The intestinal microbes possessed by a living body may be classified for each individual, and these microbes are known to be involved in various metabolisms in the intestinal tracts. In particular, the intestinal microbes related to obesity are one of the well-known fields, and it has been reported that obese people have intestinal microbes abundantly involved in metabolism of carbohydrates, fats, amino acids and the like. In addition, substances such as butyrate or acetate, which are produced by metabolism of intestinal microbes, are important factors for the immunity of the intestinal tracts and are also known to protect the living body from infection with pathogens through regulation of helper T cell production or reaction with G-protein receptor 43 (GPR43), etc. Furthermore, the intestinal microbes have been pointed out as the cause of various diseases in addition to those in the large intestine such as inflammatory bowel disease or colon cancer.

In a recent study on the human body, a study was attempted to find a correlation between hormone levels and intestinal microbes in pre-menopausal and post-menopausal women, but the study simply confirmed the degree of decrease in the total number of microbes rather than figuring out a specific change in microbes.

However, this study indicates that a hormonal change causes a change in intestinal microbes, thus reporting that the intestinal microbes have an influence on regulating estrogen in the living body through enterohepatic circulation.

A high level of estrogen in vivo is known to increase the incidence of breast cancer, and a low level of estrogen is known to increase the incidence of osteoporosis, and thus it is considered important to control an appropriate level of estrogen in the body. However, this control becomes a difficult problem in women's menopause. Accordingly, there is a need for research to regulate estrogen, a kind of female hormone, through the interaction between the living body and intestinal microbes, and further treat women's menopausal disorders and alleviate menopausal symptoms.

(Sexually Transmitted Diseases, November 2006, vol 33, No. 11, 663-665;
Bacteria and the Fate of Estrogen in the Environment 2017, vol 24, Issue 6)

DETAILED DESCRIPTION OF THE INVENTION

Technical Problem

An objective of the present disclosure is to provide novel lactic acid bacteria, *Lactobacillus plantarum* and *Bifidobacterium longum*.

Another objective of the present disclosure is to provide a composition for preventing or treating female menopausal disorders, comprising novel lactic acid bacteria.

Still another objective of the present disclosure is to provide a health functional food for preventing or ameliorating female menopausal disorders, comprising novel lactic acid bacteria.

Technical Solution

In one aspect for achieving the objectives, the present disclosure provides *Lactobacillus plantarum* NK3 (depository institution: the Korean Culture Center of Microorganisms (KCCM), date of deposit: Aug. 4, 2017, and accession number: KCCM12089P).

The *Lactobacillus plantarum* NK3 of the present disclosure has a feature of being a novel lactic acid bacterium of *Lactobacillus plantarum*, which is isolated and identified from kimchi, which is a traditional fermented food.

A 16S rDNA sequence for identification and classification of *Lactobacillus plantarum* NK3 of the present disclosure is the same as SEQ ID NO: 1 attached to the present specification. Thus, the *Lactobacillus plantarum* NK3 of the present disclosure may include the 16S rDNA of SEQ ID NO: 1.

As a result of analyzing the 16S rDNA sequence of SEQ ID NO: 1, this sequence was 99% homologous to that of generally known *Lactobacillus plantarum* strains, thus showing a highest molecular phylogenetic relationship with *Lactobacillus plantarum*. Thus, the lactic acid bacterium was identified as *Lactobacillus plantarum*, which was then named as *Lactobacillus plantarum* NK3, and deposited to the KCCM on Aug. 4, 2017 (accession number: KCCM12089P).

The *Lactobacillus plantarum* NK3 of the present disclosure is a gram-positive bacterium and a cellular form thereof is *bacillus*. More specifically, the physiological properties of *Lactobacillus plantarum* NK3 may be analyzed according to a conventional method in the art, and the results thereof are as shown in table 2 below. Specifically, *Lactobacillus plantarum* NK3 may use the followings as a carbon source: L-arabinose, D-ribose, D-galactose, D-glucose, D-fructose, D-mannose, mannitol, sorbitol, α-methyl-D-mannoside, N-acetyl-glucosamine, amygdaline, arbutin, esculin, salicin, cellobiose, maltose, lactose, melibiose, sucrose, trehalose, melezitose, gentiobiose, D-turanose, and gluconate.

In another aspect for achieving the objectives, the present disclosure provides *Bifidobacterium longum* NK49 (depository institution: the Korean Culture Center of Microorganisms (KCCM), date of deposit: Aug. 4, 2017, and accession number: KCCM12088P).

The *Bifidobacterium longum* NK49 of the present disclosure has a feature of being a novel lactic acid bacterium of *Bifidobacterium longum*, which is isolated and identified from human feces.

A 16S rDNA sequence for identification and classification of *Bifidobacterium longum* NK49 of the present disclosure is the same as SEQ ID NO: 2 attached to the present specification. Thus, *Bifidobacterium longum* NK49 of the present disclosure may include the 16S rDNA of SEQ ID NO: 2.

As a result of analyzing the 16S rDNA sequence of SEQ ID NO: 2, this sequence was 99% homologous to that of generally known *Bifidobacterium longum* strains, thus showing a highest molecular phylogenetic relationship with *Bifidobacterium longum*. Thus, the lactic acid bacterium was identified as *Bifidobacterium longum*, which was then named as *Bifidobacterium longum* NK49, and deposited to the KCCM on Aug. 4, 2017 (accession number: KCCM12088P).

The *Bifidobacterium longum* NK49 of the present disclosure is a gram-positive bacterium and a cellular form thereof is *bacillus*. More specifically, the physiological properties of *Bifidobacterium longum* NK49 may be analyzed according to a conventional method in the art, and the results thereof are as shown in table 3 below. Specifically, *Bifidobacterium longum* NK49 may use the followings as a carbon source: L-arabinose, D-ribose, D-xylose, D-galactose, D-glucose, D-fructose, mannitol, sorbitol, α-methyl-D-glucoside, esculin, salicin, maltose, lactose, melibiose, sucrose, raffinose and D-turanose.

In another aspect for achieving the objectives, the present disclosure provides a pharmaceutical composition for preventing or treating female menopausal disorders, comprising *Lactobacillus plantarum* NK3 KCCM12089P, *Bifidobacterium longum* NK49 KCCM12088P or a mixture thereof.

In the present disclosure, "female menopausal disorder" refers to all diseases that occur at the time of menopause, which appears as a sign of loss of female reproductive functions. When menopause comes, the amount or cycle of menstruation becomes irregular due to a loss of ovarian functions, and the menstruation is abolished due to a decrease in the secretion of follicle hormone (estrogen) over several months to three years, which results in acting on the autonomic nerve center of the interbrain and causing the atrophy of the autonomic nervous system, thereby causing menopausal disorders. In addition, the malfunction of the anterior pituitary gland accelerates adrenal cortical functions to cause masculinization, and the influence of thyroid hormones leads to the abnormality of the thyroid gland functions, thus resulting in a malfunction peculiar to menopause, such as causing obesity, etc. For example, this malfunction may lead to symptoms such as a hot flush, palpitation (heart beating more severe than usual, causing the heart to rumble), dizziness, tinnitus, high blood pressure, digestive troubles, headache, memory loss, depression, etc., as well as weight gain, obesity, osteoporosis, etc.

Specifically, the *Lactobacillus plantarum* NK3 and *Bifidobacterium longum* NK49 strains contained in the pharmaceutical composition of the present disclosure may be mixed at a ratio of 1:1 to 4:1 colony forming unit (CFU), but are not limited thereto.

In one example of the present disclosure, it was confirmed that each of *Lactobacillus plantarum* NK3 or *Bifidobacterium longum* NK49 strains as well as a mixture of those strains have an effect on female menopausal disorders, and in particular it was confirmed that a mixture in which *Lactobacillus plantarum* NK3 and *Bifidobacterium longum* NK49 strains are mixed at a ratio of 1:1 to 4:1 CFU shows an effect of ameliorating the indices of osteoporosis at a level similar to the positive control group dosed with estradiol similar to estrogen (FIGS. 1 to 3, and Table 4), and shows an effect of ameliorating the indices of obesity (FIGS. 4 to 5, and Table 6).

The "*Lactobacillus plantarum* NK3" of the present disclosure is the same as described above.

Specifically, the *Lactobacillus plantarum* NK3 and *Bifidobacterium longum* NK49 KCCM12088P contained in the pharmaceutical composition of the present disclosure may be a live bacterial body thereof, a dead bacterial body thereof, a culture thereof, a lysate thereof, or an extract thereof, respectively, but any type of *Lactobacillus plantarum* NK3 may be used without limitation, as long as it may achieve a preventive or therapeutic effect on female menopausal disorders.

In the present disclosure, the term "live bacterial body" may refer to a bacterial body, which is alive, and "dead bacterial body" may mean a bacterial body, which is sterilized by tyndallization, heating, pressurization, drug treatment, etc.

In the present disclosure, the term "culture" may also refer to a product obtained by culturing lactic acid bacteria in a generally known liquid or solid medium, and may be a concept of encompassing novel lactic acid bacteria in the present disclosure.

In the present disclosure, the term "lysate" may also refer to a hydrolyzate obtained by modifying the live or dead bacterial body or a product obtained by lysing the live or dead bacterial body through chemical or physical force such as homogenization, ultrasonic sonication, etc.

In the present disclosure, the term "extract" may also refer to a product obtained by extracting a live bacterial body, a dead bacterial body, a lysate thereof, a culture thereof, or a mixture thereof through various extraction methods known in the art, and is a concept of encompassing all the materials which may be obtained by processing or treating the resulting extract through other methods after the extraction.

The "*Bifidobacterium longum* NK49" of the present disclosure is the same as described above.

Specifically, the *Bifidobacterium longum* NK49 contained in the pharmaceutical composition of the present disclosure may be a live bacterial body thereof, a dead bacterial body thereof, a culture thereof, a lysate thereof, or an extract thereof, but any type of *Lactobacillus plantarum* NK3 may be used without limitation, as long as it may achieve a preventive or therapeutic effect on female menopausal disorders.

In the present disclosure, female menopausal disorders may include vasomotor symptoms such as sweating, facial flushing and the like; mental diseases such as depression, anxiety and the like; urinary diseases such as vaginal dryness, vaginal atrophy, urinary incontinence and the like; metabolic diseases such as obesity, hypertension, diabetes and the like; skin aging, and osteoporosis, and specifically osteoporosis, obesity, or depression, but are not limited thereto.

In one example of the present disclosure, as a result of administering *Lactobacillus plantarum* NK3, *Bifidobacterium longum* NK49 or a mixture thereof to an animal model with induced osteoporosis, it was confirmed that the weight of the womb and the thighbone is increased at a level similar to the group dosed with estradiol similar to estrogen (FIGS. 1 and 2), while the length of the thighbone is returned to be similar to the normal group (FIG. 3). It was also confirmed that an alkaline phosphatase (AP) enzyme activity occurs at a level similar to the group dosed with estradiol and the activity of AP enzyme, the concentration of osteocalcin, phosphorus, and calcium is returned to be similar to that of the normal group in comparison with the control group of an animal model with removed ovaries.

In addition, in one example of the present disclosure, as a result of administering *Lactobacillus plantarum* NK3, *Bifidobacterium longum* NK49 or a mixture thereof to an animal model with induced obesity, it was shown that a weight loss occurs at a level similar to the group dosed with estradiol, and it was confirmed that the expression of SREBP-1c is inhibited and the expression of PGC-1α is induced along with the activity of AMPK (FIG. 5) in comparison with the control group of the animal model with removed ovaries, thereby confirming that obesity is inhibited (Table. 6).

Furthermore, in one example of the present disclosure, as a result of administering *Lactobacillus plantarum* NK3, *Bifidobacterium longum* NK49 or a mixture thereof to a restraint stress-induced depressive animal model, it was confirmed that a concentration of corticosterone, which is a hormone induced by stress, is decreased (FIG. 6) and the behavioral indices of depressive symptoms is ameliorated (FIGS. 7 to 9), thereby showing an effect on depression.

The above results suggest that novel lactic acid bacteria and a mixture thereof according to the present disclosure have an effect of treating and ameliorating female menopausal disorders at a level similar to estrogen.

The pharmaceutical composition according to the present disclosure may be prepared into a pharmaceutical dosage form by using a method well known in the art, so as to provide a fast, suspended or prolonged release of an active ingredient thereof after being administered into a mammal. When preparing a dosage form, the pharmaceutical composition according to the present disclosure may further contain a pharmaceutically acceptable carrier, to the extent that this carrier does not suppress an activity of novel lactic acid bacteria.

The pharmaceutically acceptable carrier may include conventionally used ones, for example, lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil and the like, but is not limited thereto. In addition, the pharmaceutical composition of the present disclosure may contain a diluent or an excipient such as filler, extender, binder, humectant, disintegrant, surfactant, etc., or other pharmaceutically acceptable additives.

A dosage of the pharmaceutical composition according to the present disclosure needs to be a pharmaceutically effective amount. The "pharmaceutically effective amount" may refer to an amount sufficient to prevent or treat female menopausal disorders at a reasonable benefit/risk ratio applicable to medical treatment. An effective dose level may be variously selected by those skilled in the art depending on factors such as a formulation method, a patient's condition and weight, the patient's gender, age and degree of disease, a drug form, an administration route and period, an excretion rate, reaction sensitivity, etc. The effective amount may vary depending on a route of disposal, a use of excipient, and possibility of being used with other drugs, as recognized by those skilled in the art.

However, in case of a preparation for oral administration to achieve a preferable effect, the composition of the present disclosure may be generally administered into an adult in an amount of 0.0001 to 100 mg/kg a day, preferably 0.001 to 100 mg/kg a day based on 1 kg of body weight. When the preparation is administered as above, *Lactobacillus plantarum* NK3, *Bifidobacterium longum* NK49 or a mixture thereof according to the present disclosure may be administered in an amount of $1\times10^2$ CFU/kg to $1\times10^{11}$ CFU/kg a day. This administration may be done once a day or several times a day by dividing the preparation. The dosage does not limit the scope of the present disclosure in any aspect.

The pharmaceutical composition of the present disclosure may be administered to mammals such as mice, livestock, humans, etc. through various routes. Specifically, the pharmaceutical composition of the present disclosure may be orally or parenterally administered (for example, applied or injected intravenously, subcutaneously or intraperitoneally), but may be preferably orally administered. A solid preparation for oral administration may include powder, granule, tablet, capsule, soft capsule, pill, etc. A liquid preparation for oral administration may include a suspending agent, liquid for internal use, emulsion, syrup, aerosol, etc., but may also include various excipients, for example, humectant, sweetening agent, flavoring agent, preservative, etc. in addition to water and liquid paraffin, which are frequently used simple diluents. A preparation for parenteral administration may be used by being formulated into a dosage form of external preparation and sterilized injectable preparation such as sterilized aqueous solution, liquid, non-aqueous solvent, suspending agent, emulsion, eye drop, eye ointment, syrup, suppository, aerosol, etc., according to respective conventional methods, and preferably may be used by preparing a pharmaceutical composition of cream, gel, patch, spray, ointment, plaster, lotion, liniment, eye ointment, eye drop, paste or cataplasma, but is not limited thereto. A preparation for local administration may be an anhydrous or aqueous form depending on a clinical prescription. As the non-aqueous solvent and the suspending agent, propylene glycol, polyethylene glycol, vegetable oil like olive oil, injectable ester like ethyl oleate, etc. may be used. A base of the suppository may include witepsol, macrogol, tween 61, cacao butter, laurinum, glycerogelatin, etc.

In another aspect for achieving the objectives, the present disclosure provides a method for preventing or treating female menopausal disorders, comprising a step of administering *Lactobacillus plantarum* NK3, *Bifidobacterium longum* NK49 or a mixture thereof into a subject.

In the present disclosure, the terms "*Lactobacillus plantarum* NK3," "*Bifdobacterium longum* NK49," "administration," "mixing ratio of the novel strains," "female menopausal disorders" and the like are the same as described above.

The subject may refer to an animal, and may be typically a mammal, on which treatment using the novel lactic acid bacteria of the present disclosure may show a beneficial effect. A preferable example of this subject may include primates like humans. In addition, these subjects may include all the subjects having a symptom of female menopausal disorders, or having a risk of having the symptom.

In another aspect, the present disclosure provides a health functional food for preventing or ameliorating female menopausal disorders, containing *Lactobacillus plantarum* NK3 KCCM12089P, *Bifidobacterium longum* NK49 KCCM12088P or a mixture thereof.

In the present disclosure, the terms "*Lactobacillus plantarum* NK3," "*Bifidobacterium longum* NK49," "mixing ratio of the novel strains," "female menopausal disorders" and the like are the same as described above.

The health functional food, which puts an emphasis on a body modulating function of food, is a food, which is given value added to work and express for a particular purpose by using a physical, biochemical or bioengineering method. An ingredient of this health functional food is designed and processed to fully exert a body modulating function in vivo, which is involved in defending a living body, adjusting a body rhythm, preventing a disease and recovering from the disease, and may contain food supplementary additives, sweeteners or functional raw materials, which are acceptable as food.

In case of using *Lactobacillus plantarum* NK3 or *Bifidobacterium longum* NK49 of the present disclosure as a health functional food (or health functional beverage additive), the novel lactic acid bacteria may be added thereto per se, used along with other food or food ingredients, or appropriately used according to a conventional method. A mixed amount of the *Lactobacillus plantarum* NK3 or *Bifidobacterium longum* NK49 may be appropriately determined depending on a purpose of use thereof (prevention, health, improvement or therapeutic action).

The health functional food may contain various nutrients, vitamins, minerals (electrolytes), flavoring agents such as synthetic flavoring agents, natural flavoring agents and the like, coloring agents and enhancers (cheese, chocolate, etc.), pectic acid and salts thereof, organic acid, protective colloidal thickeners, pH adjusting agents, stabilizers, preservatives, glycerin, alcohol, carbonators used in carbonated beverages, etc. In addition, the health functional food of the present disclosure may contain pulp for preparing fruit and vegetable based beverages. These ingredients may be used alone or in combination, and a ratio of the additives is generally selected within a range of 0.001 to 50 parts by weight based on a total weight of the composition.

A type of the health functional food has no particular limitation. Food, to which the *Lactobacillus plantarum* NK3 or *Bifidobacterium longum* NK49 may be added, may include sausage, meats, bread, chocolates, snacks, candies, confectionery, ramen, pizza, other noodles, chewing gums, dairy products including ice creams, various soups, beverages, teas, health drinks, alcohol beverages, vitamin complexes and the like. In case of being formulated into beverages, liquid ingredients, which are added to the beverages in addition to the novel lactic acid bacteria, may include various flavoring agents, natural carbohydrates or the like as an additional ingredient just as contained in conventional beverages, but are not limited thereto. The aforementioned natural carbohydrates may be monosaccharide (e.g., glucose, fructose, etc.), disaccharide (e.g., maltose, sucrose, etc.) and polysaccharide (e.g., conventional sugar such as dextrin, cyclodextrin, etc.), as well as sugar alcohol such as xylitol, sorbitol, erythritol, etc.

In another aspect, the present disclosure provides a use of *Lactobacillus plantarum* NK3 KCCM12089P, *Bifidobacterium longum* NK49 KCCM12088P or a mixture thereof in the manufacture of a medicament for treating female menopausal disorders.

In another aspect, the present disclosure provides a composition for a use in treatment female menopausal disorders comprising *Lactobacillus plantarum* NK3 KCCM12089P, *Bifidobacterium longum* NK49 KCCM12088P or a mixture thereof.

In another aspect, the present disclosure provides a use of *Lactobacillus plantarum* NK3 KCCM12089P, *Bifidobacterium longum* NK49 KCCM12088P or a mixture thereof for treating female menopausal disorders.

In the present disclosure, the terms "*Lactobacillus plantarum* NK3," "*Bifidobacterium longum* NK49," "a live bacterial body, a dead bacterial body, a culture, a lysate or an extract of the strains," "a mixing ratio of the strains," "female menopausal disorders" and the like are the same as described above.

The numerical values described in the present specification as above should be interpreted to include a range of equivalents thereof, unless otherwise stated.

Advantageous Effects

*Lactobacillus plantarum* NK3, *Bifidobacterium longum* NK49, or a mixture thereof, which is a novel lactic acid bacterium according to the present disclosure, has an excellent therapeutic effect on female menopausal disorders. Thus, the novel lactic acid bacteria according to the present disclosure may be used as a composition for preventing or treating female menopausal disorders.

BRIEF DESCRIPTION OF THE DRAWINGS

The LP in drawings indicates the results of *Lactobacillus plantarum* NK3, while the BP indicates the results of *Bifidobacterium longum* NK49.

MODE FOR INVENTION

Figure 1:
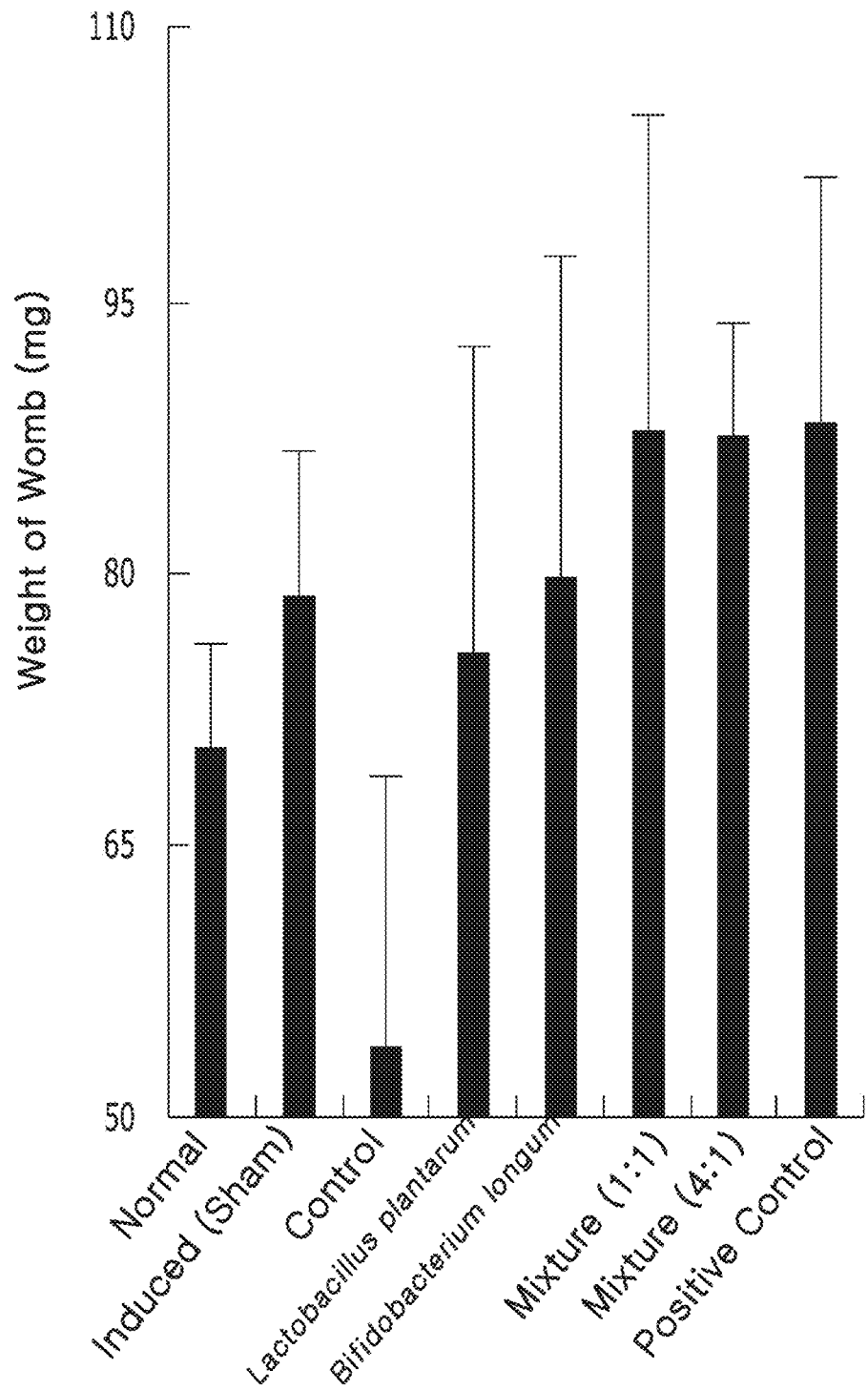
FIG. 1 is a graph showing an effect of increasing the weight of the womb with regard to *Lactobacillus plantarum* NK3, *Bifidobacterium longum* NK49 and a mixture thereof, which are novel lactic acid bacteria.

Hereinafter, the present disclosure will be described in detail through preferred Examples for better understanding of the present disclosure. However, the following Examples are provided only for the purpose of illustrating the present disclosure, and thus the present disclosure is not limited thereto.

Example 1: Isolation and Identification of Lactic Acid Bacteria (1) Isolation of Lactic Acid Bacteria from Human Feces Human feces were placed and suspended in GAM liquid medium (GAM broth; Nissui Pharmaceutical, Japan). After that, supernatant was taken and transplanted into BL agar medium (Nissui Pharmaceutical, Japan), and then anaerobically incubated at 37° C. for about 48 hours, after which colony-forming strains were isolated therefrom.

(2) Isolation of Lactic Acid Bacteria from Kimchi

Cabbage kimchi, radish kimchi or green onion kimchi was crushed respectively, after which crushed supernatant was taken and transplanted into MRS agar medium (Difco, USA), and then anaerobically incubated at 37° C. for about 48 hours, after which colony-forming strains were isolated therefrom.

(3) Identification of Isolated Lactic Acid Bacteria

Physiological properties and 16S rDNA sequences of the strains isolated from human feces or kimchi were analyzed to identify species of the strains, and then names were given to the strains. Strain names given to lactic acid bacteria are the same as shown in table 1 below. Specifically, the lactic acid bacteria isolated from kimchi were five species of *Lactobacillus plantarum* (Nos. 1 to 5 of table 1), five species of *Lactobacillus brevis* (Nos. 6 to 10 of table 1), five species of *Lactobacillus sakei* (Nos. 11 to 15 of table 1), and five species of *Lactobacillus curvatus* (Nos. 16 to 20 of table 1). The lactic acid bacteria isolated from human feces were five species of *Lactobacillus rhamnosus* (Nos. 21 to 25 of table 1), five species of *Lactobacillus plantarum* (Nos. 26 to 30 of table 1), five species of *Lactobacillus reuteri* (Nos. 31 to 35 of table 1), four species of *Lactobacillus johnsonii* (Nos. 36 to 39 of table 1), three species of *Lactobacillus* mucosae (Nos. 40 to 42 of table 1), three species of *Bifidobacterium adolescentis* (Nos. 43 to 45 of table 1), and five species of *Bifidobacterium longum* (Nos. 46 to 50 of table 1).

TABLE 1

| No. | Strain Name |
| --- | --- |
| 1 | Lactobacillus plantarum NK1 |
| 2 | Lactobacillus plantarum NK2 |
| 3 | Lactobacillus plantarum NK3 |
| 4 | Lactobacillus plantarum NK4 |
| 5 | Lactobacillus plantarum NK5 |
| 6 | Lactobacillus brevis NK6 |
| 7 | Lactobacillus brevis NK7 |
| 8 | Lactobacillus brevis NK8 |
| 9 | Lactobacillus brevis NK9 |
| 10 | Lactobacillus brevis NK10 |
| 11 | Lactobacillus sakei NK11 |
| 12 | Lactobacillus sakei NK12 |
| 13 | Lactobacillus sakei NK13 |
| 14 | Lactobacillus sakei NK14 |
| 15 | Lactobacillus sakei NK15 |
| 16 | Lactobacillus curvatus NK16 |
| 17 | Lactobacillus curvatus NK17 |
| 18 | Lactobacillus curvatus NK18 |
| 19 | Lactobacillus curvatus NK19 |
| 20 | Lactobacillus curvatus NK20 |
| 21 | Lactobacillus rhamnosus NK21 |
| 22 | Lactobacillus rhamnosus NK22 |
| 23 | Lactobacillus rhamnosus NK23 |
| 24 | Lactobacillus rhamnosus NK24 |
| 25 | Lactobacillus rhamnosus NK25 |
| 26 | Lactobacillus plantarum NK26 |
| 27 | Lactobacillus plantarum NK27 |
| 28 | Lactobacillus plantarum NK28 |
| 29 | Lactobacillus plantarum NK29 |
| 30 | Lactobacillus plantarum NK30 |
| 31 | Lactobacillus reuteri NK31 |
| 32 | Lactobacillus reuteri NK32 |
| 33 | Lactobacillus reuteri NK33 |
| 34 | Lactobacillus reuteri NK34 |
| 35 | Lactobacillus reuteri NK35 |
| 36 | Lactobacillus johnsonii NK36 |

TABLE 1-continued

| No. | Strain Name |
| --- | --- |
| 37 | Lactobacillus johnsonii NK37 |
| 38 | Lactobacillus johnsonii NK38 |
| 39 | Lactobacillus johnsonii NK39 |
| 40 | Lactobacillus mucosae NK40 |
| 41 | Lactobacillus mucosae NK41 |
| 42 | Lactobacillus mucosae NK42 |
| 43 | Bifidobacterium adolescentis NK43 |
| 44 | Bifidobacterium adolescentis NK44 |
| 45 | Bifidobacterium adolescentis NK45 |
| 46 | Bifidobacterium longum NK46 |
| 47 | Bifidobacterium longum NK47 |
| 48 | Bifidobacterium longum NK48 |
| 49 | Bifidobacterium longum NK49 |
| 50 | Bifidobacterium longum NK50 |

(4) Physiological Properties of Novel Lactic Acid Bacterium *Lactobacillus plantarum* NK3

Out of the strains described in above table 1, it was confirmed that *Lactobacillus plantarum* NK3 (accession number KCCM12089P) is a gram-positive *bacillus*. In addition, it was shown that 16S rDNA of *Lactobacillus plantarum* NK3 has a sequence of SEQ ID NO: 1. As a result of comparing the L6 rDNA sequence of *Lactobacillus plantarum* NK3 through BLAST search, a *Lactobacillus plantarum* strain having the same 16S rDNA sequence is not searched at all, and it was confirmed that the sequence is 99% homologous to the 6S rDNA sequence of a generally known *Lactobacillus plantarum* strain. Out of the physiological properties of *Lactobacillus plantarum* NK3, availability of carbon source was analyzed with a sugar fermentation test using API 50 CHL kit. The results thereof are as shown in table 2 below. In table 2 below, "+" indicates that the availability of carbon source is positive and "−" indicates that the availability of carbon source is negative.

TABLE 2

| Carbon Source | NK3 | Carbon Source | NK3 |
| --- | --- | --- | --- |
| CONTROL | − | Esculin | + |
| Glycerol | − | Salicin | + |
| Erythritol | − | Cellobiose | + |
| D-arabinose | − | Maltose | + |
| L-arabinose | + | Lactose | + |
| D-ribose | + | Melibiose | + |
| D-xylose | − | Sucrose | + |
| L-xylose | − | Trehalose | + |
| D-adonitol | − | Inulin | − |
| Methyl-BD-xylopyranoside | − | Melezitose | + |
| D-galactose | + | Raffinose | − |
| D-glucose | + | Starch | − |
| D-fructose | + | Glycogen | − |
| D-mannose | + | Xylitol | − |
| L-sorbose | − | Gentiobiose | + |
| Rhamnosus | − | D-turanose | + |
| Dulcitol | − | D-lyxose | − |
| Inositol | − | D-tagatose | − |
| Mannitol | + | D-fucose | − |
| Sorbitol | + | L-fucose | − |
| α-methyl-mannoside | ± | D-arabitol | − |
| α-methyl-glucoside | − | L-arabitol | − |
| N-acetyl-glucosamine | + | Gluconate | ± |
| Amygdaline | + | 2-keto-gluconate | − |
| Albutin | + | 5-keto-gluconate | − |

(5) Physiological Properties of Novel Lactic Acid Bacterium *Bifidobacterium longum* NK49

Out of the strains described in above table 1, it was confirmed that *Bifidobacterium longum* NK49 (accession number KCCM12088P) is a gram-positive *bacillus*. In addition, it was shown that 16S rDNA of *Bifidobacterium longum* NK49 has a sequence of SEQ ID NO: 2. As a result of comparing the +6 rDNA sequence of *Bifidobacterium longum* NK49 through BLAST search, a *Bifidobacterium longum* strain having the same 16S rDNA sequence is not searched at all, and it was confirmed that the sequence is 99% homologous to the 16S rDNA sequence of a generally known *Bifidobacterium longum* strain. Out of the physiological properties of *Bifidobacterium longum* NK49, availability of carbon source was analyzed with a sugar fermentation test using API 50 CHL kit. The results thereof are the same as shown in table 3 below. In table 3 below, "+" indicates that the availability of carbon source is positive and "−" indicates that the availability of carbon source is negative.

TABLE 3

| Carbon Source | NK49 | Carbon Source | NK49 |
|---|---|---|---|
| CONTROL | − | Esculin | + |
| Glycerol | − | Salicin | + |
| Erythritol | − | Cellobiose | − |
| D-arabinose | − | Maltose | + |
| L-arabinose | + | Lactose | + |
| D-ribose | + | Melibiose | + |
| D-xylose | ± | Sucrose | + |
| L-xylose | − | Trehalose | − |
| D-adonitol | − | Inulin | − |
| Methyl-BD-xylopyranoside | − | Melezitose | − |
| D-galactose | + | Raffinose | + |
| D-glucose | + | Starch | − |
| D-fructose | + | Glycogen | − |
| D-mannose | − | Xylitol | − |
| L-sorbose | − | Gentiobiose | − |
| Rhamnosus | − | D-turanose | ± |
| Dulcitol | − | D-lyxose | − |
| Inositol | − | D-tagatose | − |
| Mannitol | + | D-fucose | − |
| Sorbitol | + | L-fucose | − |
| α-methyl-mannoside | − | D-arabitol | − |
| α-methyl-glucoside | ± | L-arabitol | − |
| N-acetyl-glucosamine | − | Gluconate | − |
| Amygdaline | − | 2-keto-gluconate | − |
| Albutin | − | 5-keto-gluconate | − |

Example 2: Therapeutic Effect of Lactic Acid Bacteria on Osteoporosis in Animal Model (1) Preparation of Animal Model with Osteoporosis and Administration of Lactic Acid Bacteria An experiment was performed by using six C57BL/6 mice (female, 21-23 g and 6 weeks old) per group after being acclimated in a laboratory for one week. After the mice were anesthetized with isoflurane, the ovaries were removed therefrom to create an animal model with osteoporosis. From one week after ovarian removal, *Lactobacillus plantarum* NK3, *Bifidobacterium longum* NK49, a 1:1 mixture thereof, or a 4:1 mixture thereof (a ratio of LP:BL is 4:1 and the same as below), which is a novel lactic acid bacterium, was orally administered in a daily amount of 1×10⁹ CFU for six days a week for five weeks. In addition, 17β-estradiol (PC) was intraperitoneally administered at 10 μg/kg/day to the experimental animals of the positive control group, and the sham group and the experimental group with removed ovaries were orally dosed with physiological saline solution instead of drugs.

On the day after the administration of lactic acid bacteria was completed, the experimental animals were sacrificed, and then blood, thighbone, colon, womb, and liver were separated therefrom so as to measure osteoporosis indices.

(2) Measurement of Osteoporosis Indices

Osteocalcin in blood was measured with R&D system ELISA Kit (Minneapolis, MN, USA); Ca and P were measured with ASAN Ca-Lq Reagents and ASAN Pi-Lq Reagents of Asan Pharmaceutical Co., Ltd, respectively; and alkaline phosphatase (AP) activity was measured with Alkaline phosphatase activity colorimetric assay kit (Sigma, USA).

(3) Experimental Results

Figure 2:
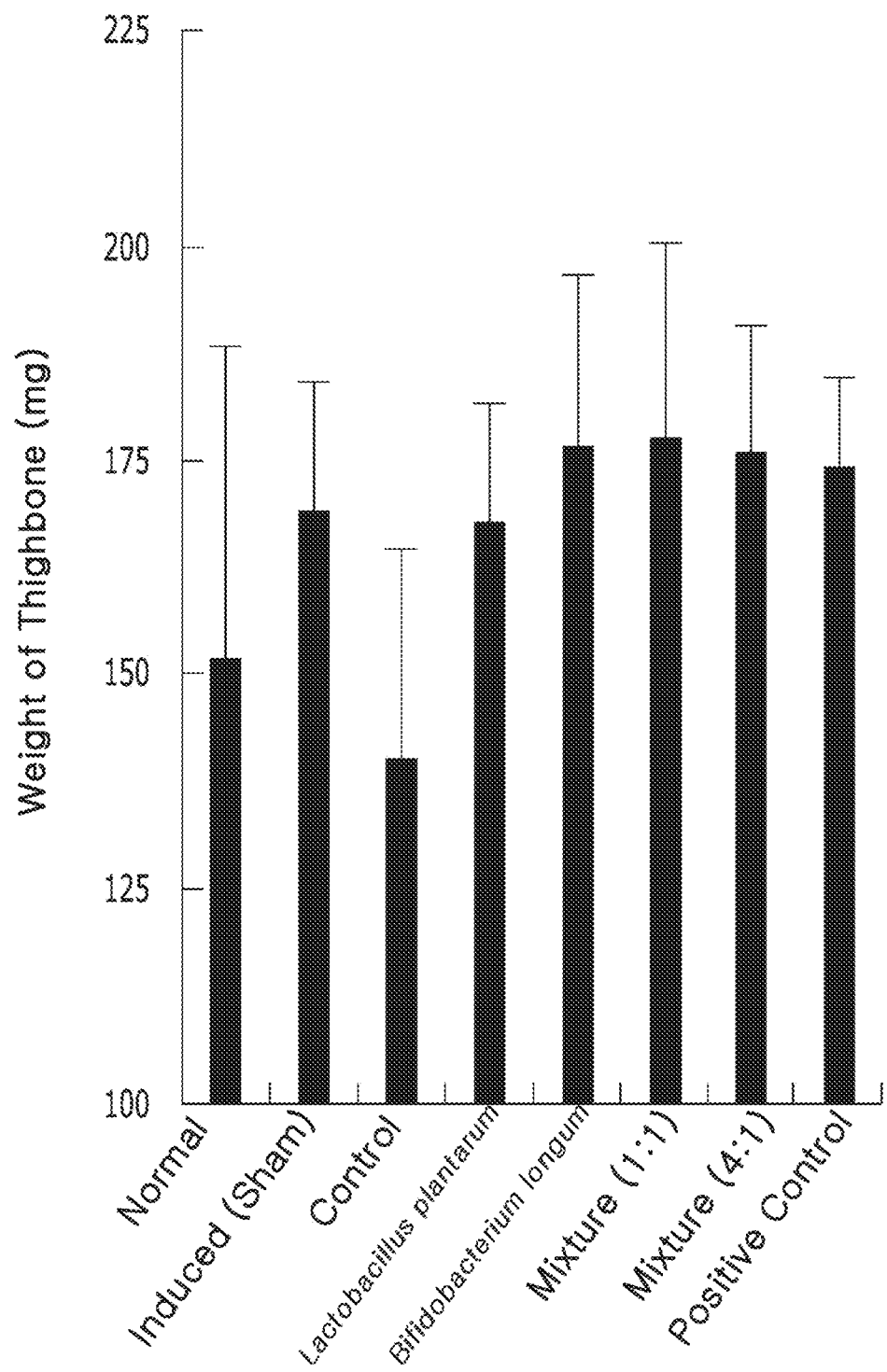
FIG. 2 is a graph showing an effect of increasing the weight of the thighbone with regard to *Lactobacillus plantarum* NK3, *Bifidobacterium longum* NK49 and a mixture thereof, which are novel lactic acid bacteria.
Figure 3:
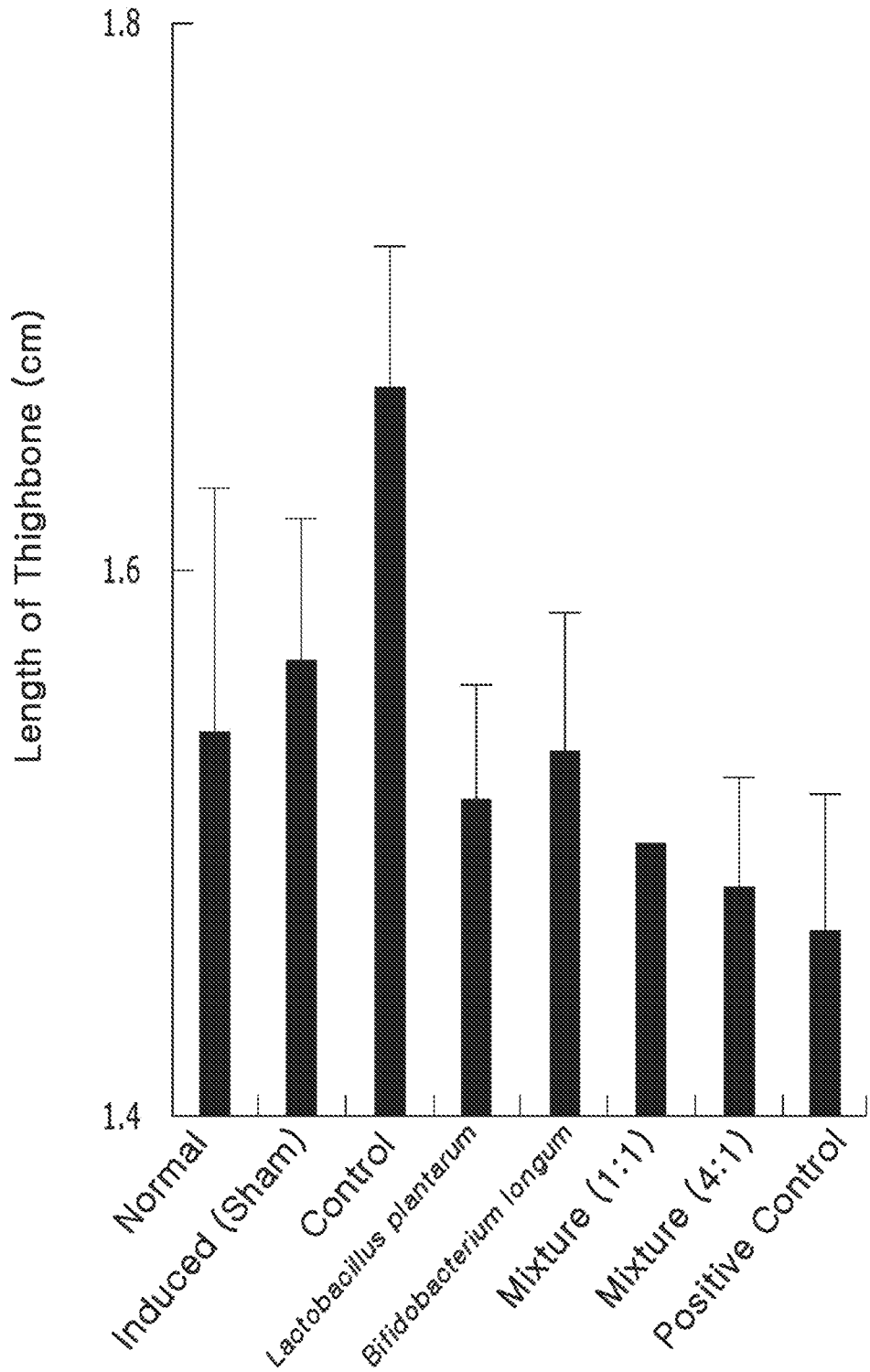
FIG. 3 is a graph showing an effect of recovering the length of the thighbone with regard to *Lactobacillus plantarum* NK3, *Bifidobacterium longum* NK49 and a mixture thereof, which are novel lactic acid bacteria.

As a result of breeding the animal model with removed ovaries as described above for six weeks, the corresponding animal model showed a decrease in the weight of the womb (FIG. 1), a decrease in the weight of the thighbone (FIG. 2), and an increase in the length of the thighbone (FIG. 3). However, with regard to the groups dosed with *Lactobacillus plantarum* NK3 (LP), *Bifidobacterium longum* NK49 (BL), a 1:1 mixture thereof (M1:1), and a 4:1 mixture thereof (LP:BL=4:1, M4:1), it was confirmed that the weight of the womb and the thighbone is increased at a level similar to the group dosed with estradiol similar to estrogen (FIGS. 1 and 2) and the length of the thighbone is recovered (FIG. 3).

In addition, as a result of breeding the animal model with removed ovaries for six weeks as described in table 4 below, the corresponding animal model tended to show an increase in alkaline phosphatase (AP) activity, an increase in the concentration of phosphorus (P) and osteocalcin, and a decrease in calcium (Ca) in blood. Meanwhile, with regard to the groups dosed with *Lactobacillus plantarum* NK3 (LP), *Bifidobacterium longum* NK49 (BL), a 1:1 mixture thereof (M1:1), and a 4:1 mixture thereof (M4:1), according to the present disclosure, it was confirmed that the activity of alkaline phosphatase (AP) and the concentration of osteocalcin, phosphorus and calcium are recovered at a level similar to the group dosed with estradiol.

TABLE 4

| | Normal group (Nor) | Induced group (Sham) | Control group (Con) | LP NK3 | BL NK49 | Mixture of lactic acid bacteria (M1:1) | Mixture of lactic acid bacteria (M4:1) | Positive control group (PC) |
|---|---|---|---|---|---|---|---|---|
| AP (IU/L) | 170.0 ± 3.4 | 174.4 ± 5.1 | 282.2 ± 10.3 | 217.2 ± 8.6 | 218.9 ± 5.1 | 215.5 ± 6.8 | 213.8 ± 8.6 | 220.6 ± 10.3 |
| Ca (mg/dL) | 6.6 ± 0.2 | 6.4 ± 0.3 | 6.4 ± 0.4 | 6.3 ± 0.3 | 6.3 ± 0.3 | 6.3 ± 0.2 | 6.2 ± 0.2 | 6.2 ± 0.2 |
| P (mg/dL) | 11.2 ± 0.2 | 11.8 ± 0.9 | 12.5 ± 1.5 | 12.1 ± 1.4 | 11.5 ± 1.2 | 11.9 ± 1.1 | 11.8 ± 0.9 | 12.1 ± 1.1 |
| Osteocalcin (μg/L) | 0.89 ± 0.2 | 0.98 ± 0.21 | 1.85 ± 0.32 | 1.46 ± 0.25 | 1.38 ± 0.15 | 1.41 ± 0.22 | 1.42 ± 0.19 | 1.53 ± 0.15 |

The above results suggest that novel lactic acid bacteria and a mixture thereof according to the present disclosure have an effect of treating osteoporosis, which is one of symptoms of female menopausal disorders, at a level similar to estrogen.

Example 3: Effect of Lactic Acid Bacteria on Ameliorating Obesity in Animal Model (1) Preparation of Animal Model with Induced Obesity and Administration of Lactic Acid Bacteria An experiment was performed by using six C57BL/6 mice (female, 21-23 g and 6 weeks old) per group after being acclimated in a laboratory for one week as described above in (1) of Example 2. After the mice were anesthetized with isoflurane and the ovaries were removed therefrom, the resulting mice were raised for six weeks so as to create an animal model with obesity, showing a significant weight gain. From one week after ovarian removal, *Lactobacillus plantarum* NK3, *Bifidobacterium longum* NK49, a 1:1 mixture thereof, or a 4:1 mixture thereof, which is a novel lactic acid bacterium, was orally administered in a daily amount of 1×109 CFU for six days a week for five weeks. In addition, 17β-estradiol (PC) was intraperitoneally administered at 10 μg/kg/day to the experimental animals of the positive control group, and the sham group and the experimental group with removed ovaries were orally dosed with physiological saline solution instead of drugs.

On the day after the administration of lactic acid bacteria was completed, the experimental animals were sacrificed, and then blood, thighbone, colon, womb, and liver were separated therefrom so as to measure obesity indices. The body weight was measured once a week.

(2) Measurement of AMPK Activity

The AMPK activity in the liver was measured by using an immunoblotting method. Specifically, the isolated liver was placed in a radio immunoprecipitation assay lysis buffer (RIPA, Pierce, Rockford, IL, USA), pulverized, and centrifuged at 10,000 g for 10 minutes so as to obtain a supernatant. This supernatant was subjected to 10% SDS-PAGE gel electrophoresis and transferred to a membrane. After reacting with antibodies of AMPK, p-AMPK and β-actin overnight at 4° C., the resulting product was subjected to a reaction with a secondary antibody and washed. Then, the resulting product was confirmed by developing color with an enhanced chemiluminescence (ECL) reagent.

(3) Measurement of SREBP-1c and PGC-1α Expression

An expression of sterol regulatory element-binding transcription factor 1c (SREBP-1c) and peroxisome proliferator-activated receptor gamma coactivator 1-alpha (PGC-1α) was measured by using a quantitative reverse transcription polymerase chain reaction (qPCR).

Specifically, mRNA was extracted from the liver isolated from the animal model by using a Qiagen mRNA extract kit, and then qPCR was performed by using SYBER premix agents with a Takara thermal cycler. Thermal cycling was performed under the following conditions by using the primers in table 5 below: A DNA polymerase activation was performed at 95° C. for 30 seconds, and then amplified repeatedly 40 times while being subjected to a reaction at 95° C. at an interval of 15 seconds and at 60° C. at an interval of 30 seconds. The amount of final expressed genes was calculated in comparison with β-actin.

TABLE 5

| SEQ ID NO | Primer | Sequence |
|---|---|---|
| 3 | SREBP-1c forward | 5'-AGC TGT CGG GGT AGC GTC TG-3' |
| 4 | SREBP-1c reverse | 5'-GAG AGT TGG CAC CTG GGC TG-3' |
| 5 | PGC-1α forward | 5'-CCG CCA CCT TCA ATC CAG AG-3' |
| 6 | PGC-1α reverse | 5'-CAA GTT CTC GAT TTC TCG ACG G-3' |
| 7 | β-actin forward | 5'-TGT CCA CCT TCC AGC AGA TGT-3' |
| 8 | β-actin reverse | 5'-AGC TCA GTA ACA GTC CGC CTA GA-3' |

(4) Experimental Results

Figure 4:
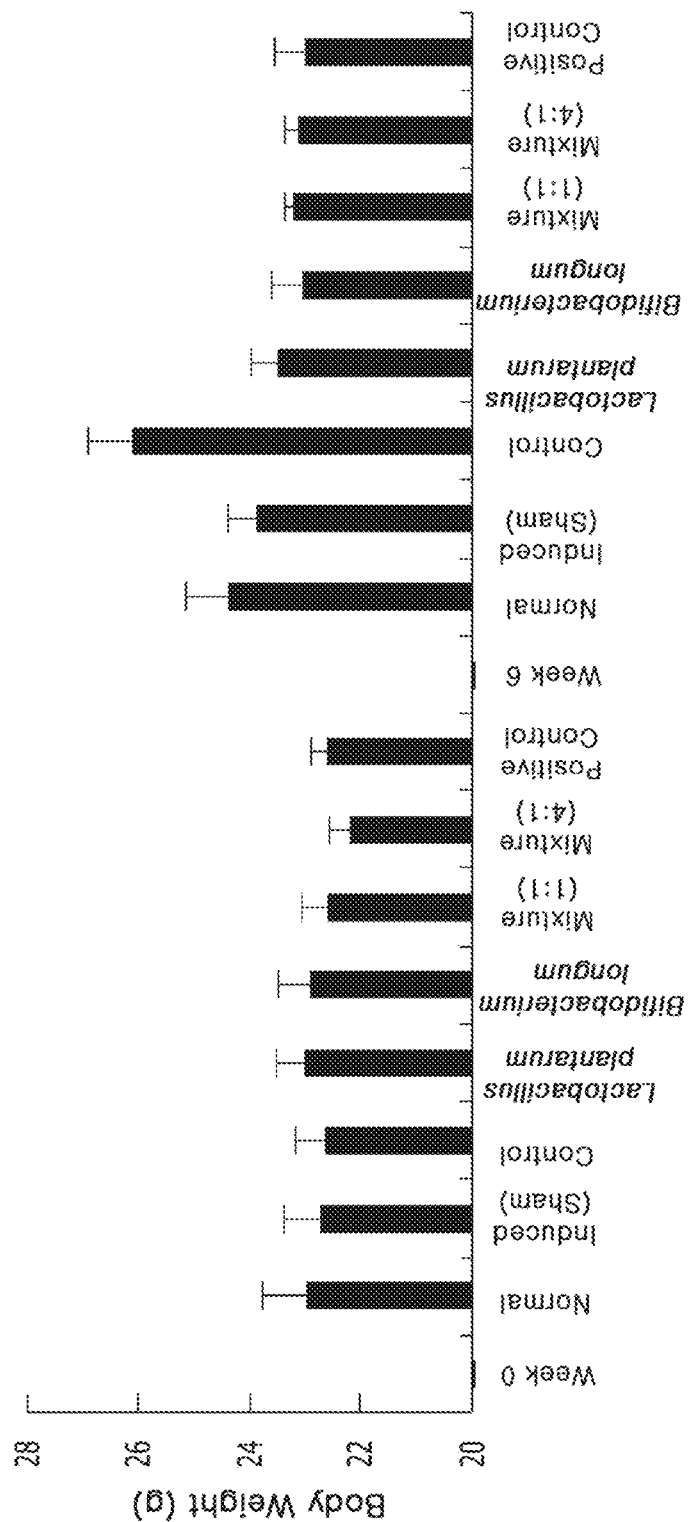
FIG. 4 is a graph showing an inhibitory capacity of obesity with regard to *Lactobacillus plantarum* NK3, *Bifidobacterium longum* NK49 and a mixture thereof, which are novel lactic acid bacteria.

As a result of breeding the animal model with removed ovaries as described above for six weeks, the corresponding animal model showed a significant weight gain. Meanwhile, with regard to the groups dosed with *Lactobacillus plantarum* NK3 (LP), *Bifidobacterium longum* NK49 (BL), a 1:1 mixture thereof (M1:1), and a 4:1 mixture thereof (M4:1) according to the present disclosure, it was confirmed that a weight loss occurs at a level similar to the group dosed with estradiol, which is in particular less than a weight gain of the normal animal without removed ovaries (FIG. 4).

Figure 5:
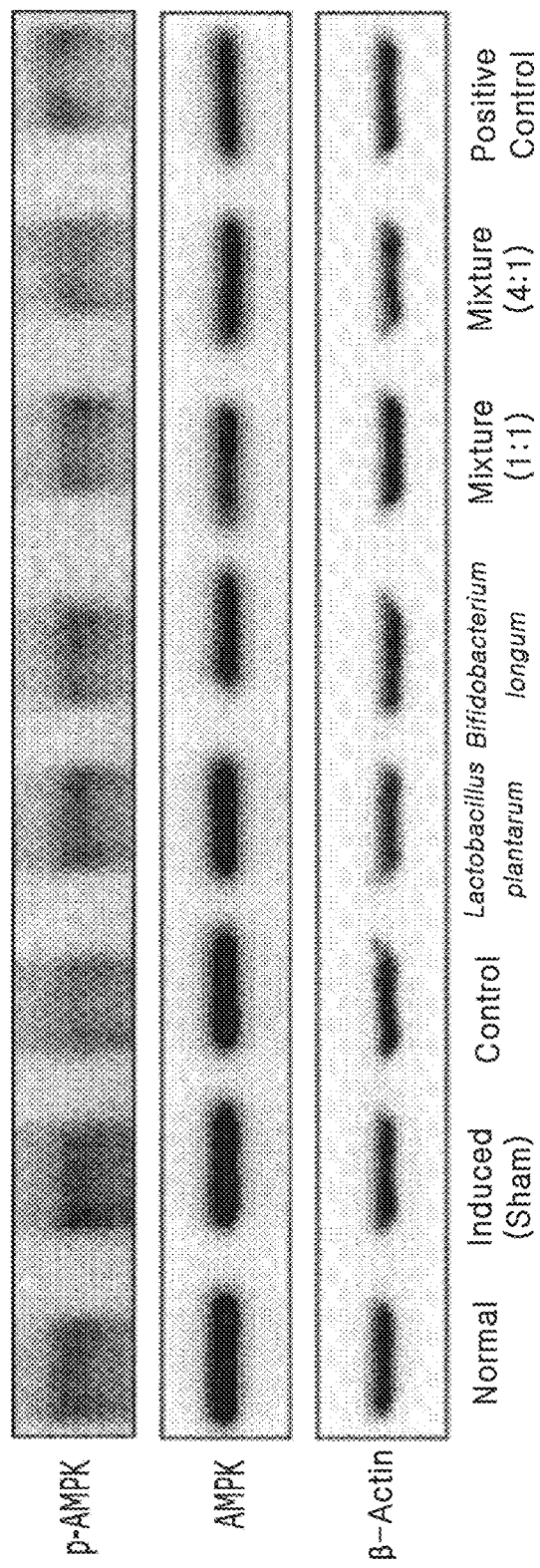
FIG. 5 is an image showing an effect of increasing the AMPK activity with regard to *Lactobacillus plantarum* NK3, *Bifidobacterium longum* NK49 and a mixture thereof, which are novel lactic acid bacteria.

In addition, as a result of breeding the animal model with removed ovaries for six weeks, the AMPK activity was decreased (FIG. 5), while the expression of SREBP-1c was induced and the expression of PGC-1α was inhibited as shown in table 6 below. However, with regard to the groups dosed with *Lactobacillus plantarum* NK3 (LP), *Bifidobacterium longum* NK49 (BL), a 1:1 mixture thereof (M1:1), and a 4:1 mixture thereof (M4:1) according to the present disclosure, the AMPK activity occurred at a level similar to the group dosed with estradiol (FIG. 5), which was higher than that of the control group with removed ovaries. In addition, it was confirmed as shown in table 6 below that the expression of SREBP-1c is inhibited and the expression of PGC-1α is induced the present disclosure compared to the mouse model with removed ovaries, thereby confirming that obesity is inhibited.

TABLE 6

|  | Normal group (Nor) | Induced group (Sham) | Control group (Con) | LP NK3 | BL NK49 | Mixture of lactic acid bacteria (M1:1) | Mixture of lactic acid bacteria (M4:1) | Positive control group (PC) |
|---|---|---|---|---|---|---|---|---|
| SREBP-1c | 1.0 ± 0.1 | 1.2 ± 0.2 | 4.5 ± 0.5 | 2.5 ± 0.6 | 2.2 ± 0.5 | 2.3 ± 0.3 | 2.4 ± 0.4 | 2.7 ± 0.3 |
| PGC-1α | 1.0 ± 0.1 | 1.1 ± 0.1 | 0.6 ± 0.2 | 0.8 ± 0.2 | 0.9 ± 0.2 | 0.8 ± 0.1 | 0.9 ± 0.2 | 0.8 ± 0.2 |

The above results suggest that novel lactic acid bacteria and a mixture thereof according to the present disclosure have an effect of ameliorating obesity or weight gain, which is one of symptoms of female menopausal disorders, at a level similar to estrogen.

Example 4: Therapeutic Effect of Lactic Acid Bacteria on Depression in Animal Model (1) Preparing of Restraint Stress-Induced Mouse Model of Depression A mouse model of depression was fixed to a 3×10 cm cylindrical-shaped restraint stress apparatus, such that the mouse may not move therein at all. Then, the mouse was given restraint stress 12 hours each for two days in a row. From the next day, *Lactobacillus plantarum* NK3, *Bifidobacterium longum* NK49, or a mixture thereof was administered (NK3, NK49, MIX: 1×10$^9$ CFU/mouse) for five days to measure the indices of depressive behaviors on the day after the final administration.

(2) Measurement of Plasma Corticosterone Concentrations

Figure 6:
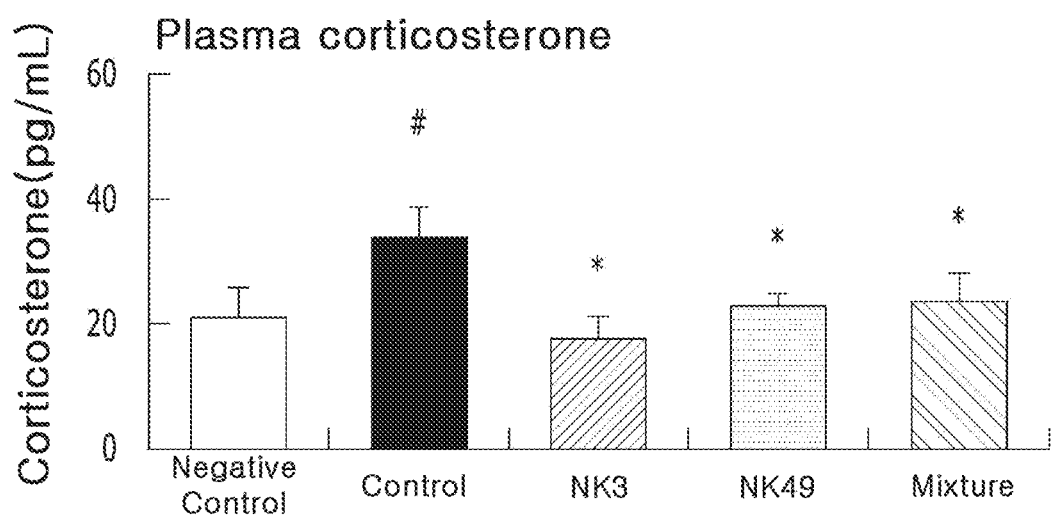
FIG. 6 is a graph showing an effect on corticosterone concentrations with regard to *Lactobacillus plantarum* NK3, *Bifidobacterium longum* NK49 and a mixture thereof, which are novel lactic acid bacteria.

With regard to the restraint stress-induced mouse model of depression prepared as above, the plasma concentration of the stress hormone corticosterone was significantly higher than that of the control group, thus confirming that the animal model is made suitable for this experiment. In case of administering *Lactobacillus plantarum* NK3, *Bifidobacterium longum* NK49, or a mixture thereof (MIX), it was confirmed that the plasma concentration of corticosterone becomes all low (FIG. 6).

(3) Elevated Plus Maze (EPM) Experiment

An elevated plus maze experimental apparatus was a black plexiglass apparatus, in which two open arms (30×7 cm) and two enclosed arms (30×7 cm) with 20 cm-high walls stand 50 cm high above a floor, each extending 7 cm away from a center platform. A mouse movement in the elevated plus maze was recorded after being placed in a room with a video camera of 20 Lux brightness installed high thereon.

Specifically, a C57BL/6 mouse (male, 19-22 g) was placed in the middle of the elevated plus maze with the head of the mouse facing toward an open arm. A time spent in open and closed arms and the number of entries thereinto were measured for five minutes. A time spent in open arms (OT) out of a total test time was calculated via [a time spent in open arms/(a time spent in open arms (OT)+a time spent in closed arms)]×100. And open arm entries (OE) were calculated via [open arm entries/(open arm entries+closed arm entries)]×100, and the results thereof are shown in FIG. 7.

Figure 7:
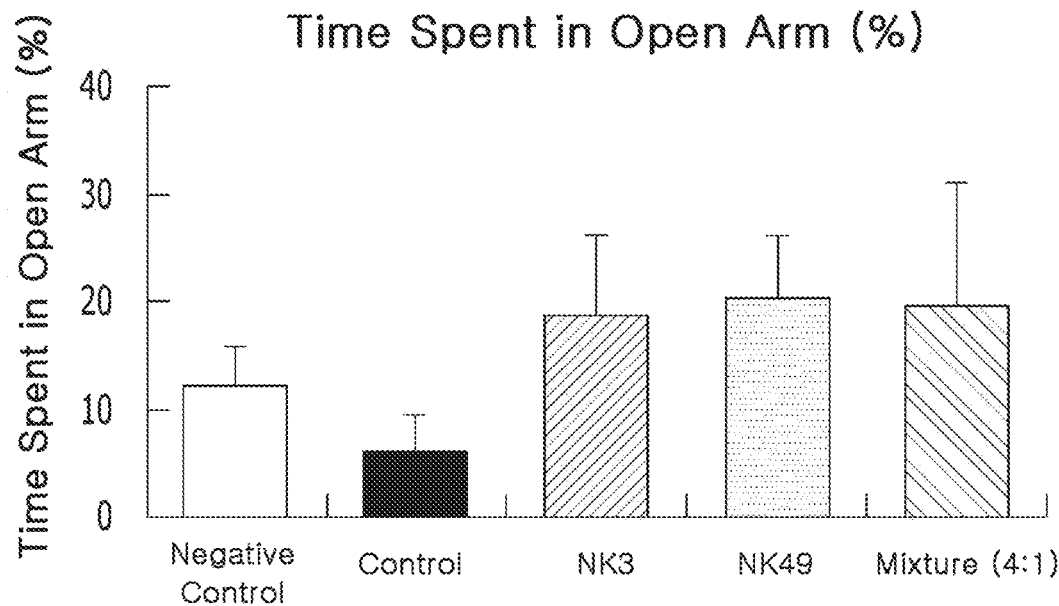
FIG. 7 is a graph showing an effect of alleviating depression through an elevated plus maze (EPM) experiment with regard to *Lactobacillus plantarum* NK3, *Bifidobacterium longum* NK49 and a mixture thereof, which are novel lactic acid bacteria.
Figure 7:
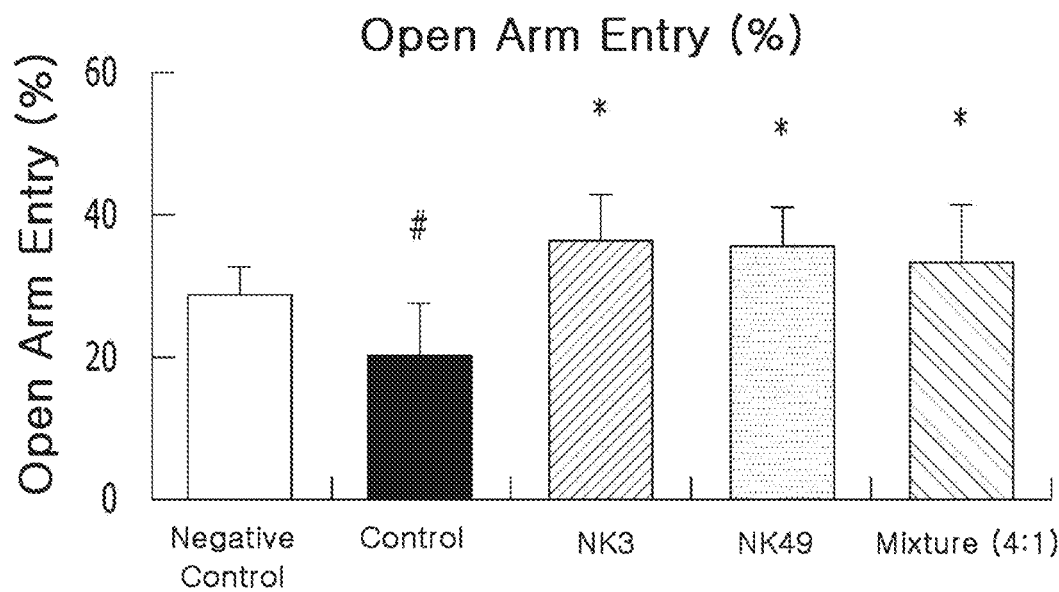

As a result of measuring a ratio of the time spent in open arms (OT) and the open arm entries (OE) as shown in FIG. 7, the groups dosed with *Lactobacillus plantarum* NK3, *Bifidobacterium longum* NK49, or a mixture thereof (MIX) showed a value significantly higher than that of the non-dosed group of mice with induced restraint stress, thus confirming that the anxiety symptoms are alleviated among the mice dosed with the strains.

(4) Forced Swimming Test (FST)

A water tank with a height of 40 cm and a diameter of 20 cm was filled up to 30 cm with water having a temperature of 25±1° C. according to the conventionally known method of Porsolt et al. (1997), after which each of the experimental mice was placed into the water tank and forced to stay there for six minutes, out of which first two minutes were considered as an adaptive time without measurement, and then for the last four minutes, an immobility time for the experimental animal was measured (in this case, the immobility means a state that the mouse is standing upright and floating in the water motionlessly except the least movement to keep its head only above the water). The results of measurement are shown in FIG. 8.

Figure 8:
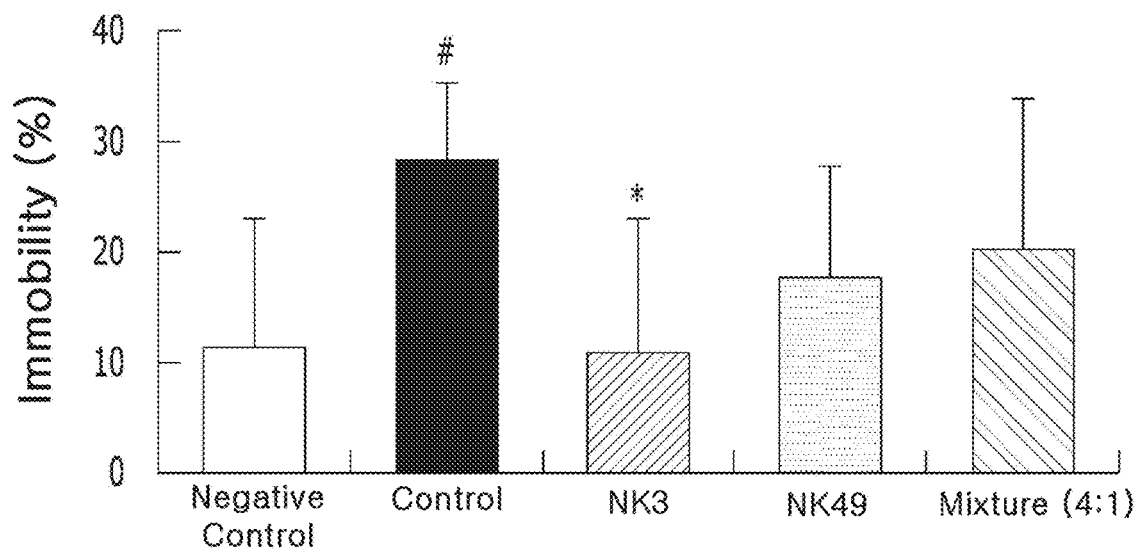
FIG. 8 is a graph showing an effect of alleviating depression through a forced swimming test (FST) with regard to *Lactobacillus plantarum* NK3, *Bifidobacterium longum* NK49 and a mixture thereof, which are novel lactic acid bacteria.

As a result of measuring a ratio of immobile mice as shown in FIG. 8, the groups dosed with *Lactobacillus plantarum* NK3, *Bifidobacterium longum* NK49, or a mixture thereof (MIX) showed a value significantly lower than that of the non-dosed group of mice with induced restraint stress, thus confirming that the sudden depressive state of the mice that give up survival is alleviated when being dosed with the strains.

(5) Tail Suspension Test (TST)

According to the conventionally known method of Steru et al. (1985), a fixture was attached about 1 cm to the end of the tail of the mouse, and then hung 50 cm away from the ground. Then, an immobility time for the experimental animal was measured for a total of six minutes and the results thereof are shown in FIG. 9.

Figure 9:
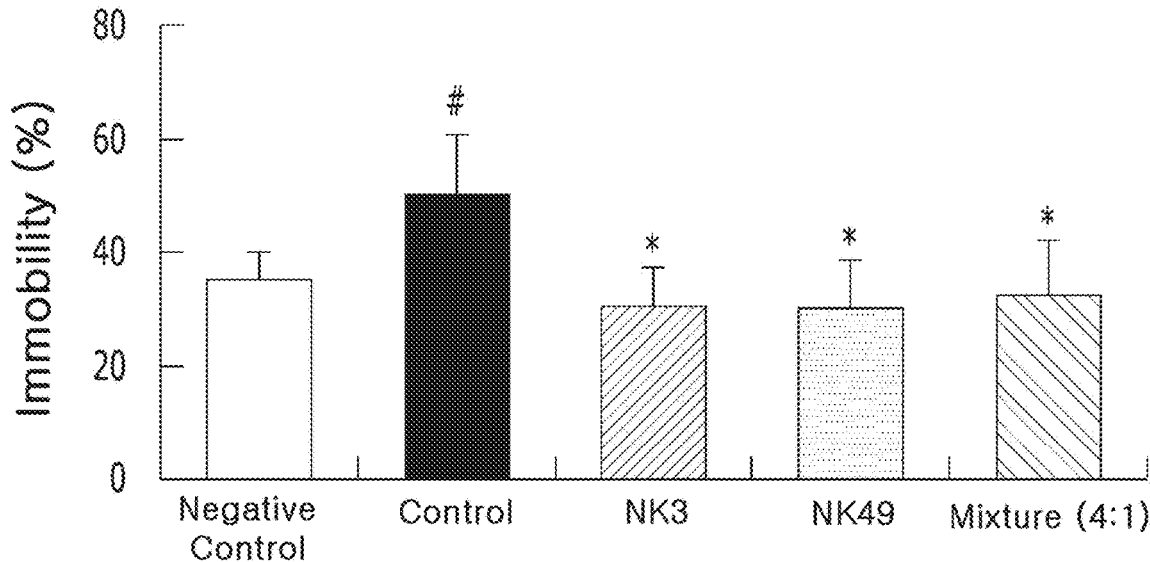
FIG. 9 is a graph showing an effect of alleviating depression through a tail suspension test (TST) with regard to *Lactobacillus plantarum* NK3, *Bifidobacterium longum* NK49 and a mixture thereof, which are novel lactic acid bacteria.

As a result of measuring a ratio of immobile mice as shown in FIG. 9, the groups dosed with *Lactobacillus plantarum* NK3, *Bifidobacterium longum* NK49, or a mixture thereof (MIX) showed a value significantly lower than that of the non-dosed group of mice with induced restraint stress, thus confirming that the depressive state of the mice is alleviated when being dosed with the strains.

The above results suggest that novel lactic acid bacteria and a mixture thereof according to the present disclosure have an effect of ameliorating depression, which is one of symptoms of female menopausal disorders.

Accession Information of Lactic Acid Bacteria

The present inventors deposited *Lactobacillus plantarum* NK3 for the purpose of patent to the Korean Culture Center of Microorganisms, a certified depository institution (address: Yurim B/D, 45, Hongjenae 2ga-gil, Seodaemun-gu, Seoul, Republic of Korea) on Aug. 4, 2017, and received an accession number of KCCM12089P.

Also, the present inventors deposited *Bifidobacterium longum* NK49 for the purpose of patent to the Korean Culture Center of Microorganisms, a certified depository institution (address: Yurim B/D, 45, Hongjenae 2ga-gil, Seodaemun-gu, Seoul, Republic of Korea) on Aug. 4, 2017, and received an accession number of KCCM12088P.

INDUSTRIAL APPLICABILITY

*Lactobacillus plantarum* NK3, *Bifidobacterium longum* NK49, or a mixture thereof, which are novel lactic acid bacteria according to the present disclosure, have an effect of treating female menopausal disorders, such as treatment of osteoporosis, amelioration of obesity, or alleviation of depression, and thus may be used as a composition for preventing or treating female menopausal disorders and may be expected to be useful in a related industry field of drug medicines and foods.

The invention claimed is:

1. A method for treating a female menopausal disorder comprising administering to a subject in need thereof an effective amount of *Bifidobacterium longum* NK49 having the accession number KCCM12088P,
   wherein the subject is a female having a sign of loss of female reproductive function, and
   wherein the female menopausal disorder is at least one selected from the group consisting of depression, anxiety, obesity, and osteoporosis.

2. The method of claim 1, wherein the method further comprises administering an effective amount of *Lactobacillus plantarum* NK3 having the accession number KCCM12089P.

3. The method of claim 1, wherein the *Bifidobacterium longum* NK49 having the accession number KCCM12088P comprises a 16S rDNA sequence of SEQ ID NO: 2.

4. The method of claim 2, wherein *Lactobacillus plantarum* NK3 having the accession number KCCM12089P comprises a 16S rDNA sequence of SEQ ID NO: 1.

5. The method of claim 1, wherein the female menopausal disorder is osteoporosis, obesity, or depression.

6. The method of claim 1, the *Bifidobacterium longum* NK49 having the accession number KCCM12088P is a live bacterial body thereof, a dead bacterial body thereof, a culture thereof, a lysate thereof, or an extract thereof.

7. The method of claim 2, the *Lactobacillus plantarum* NK3 having the accession number KCCM12089P is a live bacterial body thereof, a dead bacterial body thereof, a culture thereof, a lysate thereof, or an extract thereof.

8. The method of claim 2, wherein a ratio of mixture of *Lactobacillus plantarum* NK3 having the accession number KCCM12089P and *Bifidobacterium longum* NK49 having the accession number KCCM12088P is 1:1 to 4:1 CFU.

* * * * *

```
                        SEQUENCE LISTING

<160> NUMBER OF SEQ ID NOS: 8

<210> SEQ ID NO 1
<211> LENGTH: 1436
<212> TYPE: DNA
<213> ORGANISM: Artificial Sequence
<220> FEATURE:
<223> OTHER INFORMATION: NK3 16s rDNA

<400> SEQUENCE: 1
gcaagtcgaa cgaactctgg tattgattgg tgcttgcatc atgatttaca tttgagtgag      60
tggcgaactg gtgagtaaca cgtgggaaac ctgcccagaa gcggggdata acacctggaa     120
acagatgcta ataccgcata acaacttgga ccgcatggtc cgagcttgaa agatggcttc     180
ggctatcact tttggatggt cccgcggcgt attagctaga tggtggggta atggctcacc     240
atggcaatga tacgtagccg acctgagagg gtaatcggcc acattgggac tgagacacgg     300
cccaaactcc tacgggaggc agcagtaggg aatcttccac aatggacgaa agtctgatgg     360
agcaacgccg cgtgagtgaa gaagggtttc ggctcgtaaa actctgttgt taaagaagaa     420
catatctgag agtaactgtt caggtattga cggtatttaa ccagaaagcc acggctaact     480
acgtgccagc agccgcggta atacgtaggt ggcaagcgtt gtccggattt attgggcgta     540
aagcgagcgc aggcggtttt ttaagtctga tgtgaaagcc tttcggctca accgaagaag     600
tgcatcggaa actgggaaac ttgagtgcag aagaggacag tggaactcca tgtgtagcgg     660
tgaaatgcgt agatatatgg aagaacacca gtggcgaagg cggctgtctg gtctgtaact     720
gacgctgagg ctcgaaagta tgggtagcaa acaggattag ataccctggt agtccatacc     780
gtaaacgatg aatgctaagt gttggagggt ttccgccctt cagtgctgca gctaacgcat     840
taagcattcc gcctggggag tacggccgca aggctgaaac tcaaaggaat tgacggggc     900 ccgcacaagc ggtggagcat gtggtttaat tcgaagctac gcgaagaacc ttaccaggtc     960
ttgacatact atgcaaatct aagagattag acgttccctt cggggacatg gatacaggtg    1020
gtgcatggtt gtcgtcagct cgtgtcgtga gatgttgggt taagtcccgc aacgagcgca    1080
acccttatta tcagttgcca gcattaagtt gggcactctg gtgagactgc cggtgacaaa    1140
ccggaggaag gtggggatga cgtcaaatca tcatgcccct tatgacctgg gctacacacg    1200
tgctacaatg gatggtacaa cgagttgcga actcgcgaga gtaagctaat ctcttaaagc    1260
cattctcagt tcggattgta ggctgcaact cgcctacatg aagtcggaat cgctagtaat    1320
cgcggatcag catgccgcgg tgaatacgtt cccgggcctt gtacacaccg cccgtcacac    1380
catgagagtt tgtaacaccc aaagtcggtg gggtaacctt ttaggaacca gccgcc        1436

<210> SEQ ID NO 2
<211> LENGTH: 1342
<212> TYPE: DNA
<213> ORGANISM: Artificial Sequence
<220> FEATURE:
<223> OTHER INFORMATION: NK49 16s rDNA

<400> SEQUENCE: 2
```

```
ggctttgctt ggtggtgaga gtggcgaacg ggtgagtaat gcgtgaccga cctgccccat    60
acaccggaat agctcctgga aacgggtggt aatgccggat gctccagttg atcgcatggt   120
cttctgggaa agctttcgcg gtatgggatg gggtcgcgtc ctatcagctt gacggcgggg   180
taacggccca ccgtggcttc gacgggtagc cggcctgaga gggcgaccgg ccacattggg   240
actgagatac ggcccagact cctacgggag gcagcagtgg ggaatattgc acaatgggcg   300
caagcctgat gcagcgacgc cgcgtgaggg atggaggcct cgggttgta aacctcttttt   360 atcggggagc aagcgagagt gagtttaccc gttgaataag caccggctaa ctacgtgcca   420
gcagccgcgg taatacgtag ggtgcaagcg ttatcccgga attattgggc gtaaagggct   480
cgtaggcggt tcgtcgcgtc cggtgtgaaa gtccatcgct taacggtgga tccgcgccgg   540
gtacgggcgg gcttgagtgc ggtaggggag actggaattc ccggtgtaac ggtggaatgt   600
gtagatatcg ggaagaacac caatggcgaa ggcaggtctc tgggccgtta ctgacgctga   660
ggagcgaaag cgtggggagc gaacaggatt agataccctg gtagtccacg ccgtaaacgg   720
tggatgctgg atgtggggcc cgttccacgg gttccgtgtc ggagctaacg cgttaagcat   780
cccgcctggg ggagtacggc cgcaaggcta aaactcaaag aaattgacgg gggcccgcac   840
aagcggcgga gcatgcggat taattcgatg caacgcgaag aaccttacct gggcttgaca   900
tgttcccgac ggtcgtagag atacggcttc ccttcggggc gggttcacag gtggtgcatg   960
gtcgtcgtca gctcgtgtcg tgagatgttg ggttaagtcc cgcaacgagc gcaaccctcg  1020
ccccgtgttg ccagcggatt atgccgggaa ctcacggggg accgccgggg ttaactcgga  1080
ggaaggtggg gatgacgtca gatcatcatg ccccttacgt ccagggcttc acgcatgcta  1140
caatggccgg tacaacggga tgcgacgcgg cgacgcggag cggatccctg aaaaccggtc  1200
tcagttcgga tcgcagtctg caactcgact gcgtgaaggc ggagtcgcta gtaatcgcga  1260
atcagcaacg tcgcggtgaa tgcgttcccg ggccttgtac acaccgcccg tcaagtcatg  1320
aaagtgggca gcacccgaag cc                                          1342

<210> SEQ ID NO 3
<211> LENGTH: 20
<212> TYPE: DNA
<213> ORGANISM: Artificial Sequence
<220> FEATURE:
<223> OTHER INFORMATION: SREBP-1c forward primer

<400> SEQUENCE: 3
agctgtcggg gtagcgtctg                                               20

<210> SEQ ID NO 4
<211> LENGTH: 20
<212> TYPE: DNA
<213> ORGANISM: Artificial Sequence
<220> FEATURE:
<223> OTHER INFORMATION: SREBP-1c reverse primer

<400> SEQUENCE: 4
gagagttggc acctgggctg                                               20

<210> SEQ ID NO 5
<211> LENGTH: 20
<212> TYPE: DNA
<213> ORGANISM: Artificial Sequence
<220> FEATURE:
<223> OTHER INFORMATION: PGC-1a forward primer

<400> SEQUENCE: 5
```

```
ccgccacctt caatccagag                                              20

<210> SEQ ID NO 6
<211> LENGTH: 22
<212> TYPE: DNA
<213> ORGANISM: Artificial Sequence
<220> FEATURE:
<223> OTHER INFORMATION: PGC-1a reverse primer

<400> SEQUENCE: 6
caagttctcg atttctcgac gg                                           22

<210> SEQ ID NO 7
<211> LENGTH: 21
<212> TYPE: DNA
<213> ORGANISM: Artificial Sequence
<220> FEATURE:
<223> OTHER INFORMATION: b-actin forward primer

<400> SEQUENCE: 7
tgtccacctt ccagcagatg t                                            21

<210> SEQ ID NO 8
<211> LENGTH: 23
<212> TYPE: DNA
<213> ORGANISM: Artificial Sequence
<220> FEATURE:
<223> OTHER INFORMATION: b-actin reverse primer

<400> SEQUENCE: 8
agctcagtaa cagtccgcct aga                                          23
```